US012742216B2

(12) United States Patent
Wang et al.

(10) Patent No.: US 12,742,216 B2
(45) Date of Patent: Sep. 22, 2026

(54) METHOD FOR DETERMINING TITER OF RNA VIRAL VECTORS

(71) Applicant: ABELZETA INC., Rockville, MD (US)

(72) Inventors: Zefa Wang, Shanghai (CN); Li Li, Shanghai (CN); Hanning Zhang, Shanghai (CN); Yilang Cao, Shanghai (CN); Ting Han, Shanghai (CN); Jishun Lu, Shanghai (CN); Yi Hong, Shanghai (CN); Li Zhang, Shanghai (CN)

(73) Assignee: ABELZETA INC., Rockville, MD (US)

( * ) Notice: Subject to any disclaimer, the term of this patent is extended or adjusted under 35 U.S.C. 154(b) by 714 days.

(21) Appl. No.: 18/043,804

(22) PCT Filed: Sep. 3, 2021

(86) PCT No.: PCT/US2021/049110

§ 371 (c)(1),
(2) Date: Mar. 2, 2023

(87) PCT Pub. No.: WO2022/051648

PCT Pub. Date: Mar. 10, 2022

(65) Prior Publication Data

US 2023/0304108 A1 Sep. 28, 2023

(30) Foreign Application Priority Data

Sep. 4, 2020 (CN) ......................... 202010922956.2

(51) Int. Cl.
*C12Q 1/70* (2006.01)
*C12Q 1/6844* (2018.01)

(52) U.S. Cl.
CPC ........... *C12Q 1/702* (2013.01); *C12Q 1/6844* (2013.01)

(58) Field of Classification Search
CPC .... C12Q 1/686; C12Q 1/6844; C12Q 1/6851; C12Q 1/702
See application file for complete search history.

(56) References Cited

U.S. PATENT DOCUMENTS

| | | | | |
|---|---|---|---|---|
| 5,994,136 | A | 11/1999 | Naldini et al. | |
| 6,013,516 | A | 1/2000 | Verma et al. | |
| 6,682,907 | B1 | 1/2004 | Charneau et al. | |
| 2003/0175698 | A1* | 9/2003 | Kim | C12Q 1/702 435/456 |
| 2014/0107190 | A1* | 4/2014 | Martin Molina | C12N 15/86 435/375 |
| 2018/0066325 | A1 | 3/2018 | Kelleher et al. | |
| 2018/0187184 | A1* | 7/2018 | Herholt | C12N 15/1065 |

FOREIGN PATENT DOCUMENTS

| | | | |
|---|---|---|---|
| CN | 102134613 | A | 7/2011 |
| CN | 107365875 | A | 11/2017 |
| CN | 108103245 | A | 6/2018 |
| JP | 2004520075 | A | 7/2004 |

OTHER PUBLICATIONS

Sun, B., et al., 1996, A simplified, competitive RT-PCR method for measuring rat IFN-gamma mRNA expression, J. Immunol. Meth. 195:139-148.*

Sun et al.: "A simplified, competitive RT-PCR method for measuring rat IFN-gamma mRNA expression": Journal of Immunological Methods, 1996, vol. 195, pp. 139-148.

International Search Report and Written Opinion of PCT/US2021/049110, mailed on Dec. 20, 2021.

Bell et al. "The Protein CTCF Is Required for the Enhancer Blocking Activity of Vertebrate Insulators", Cell, vol. 98:387-396; 1999. [10 pages].

Blömer et al. "Applications of gene therapy to the CNS", Human Mol Genet (1996) vol. 5, 1397-1404. [8 pages].

Blömer et al. "Highly Efficient and Sustained Gene Transfer in Adult Neurons with a Lentivirus Vector", J Virol (1997) 71(9), 6641-6649. [9 pages].

Burgess-Beusse et al. "The insulation of genes from external enhancers and silencing chromatin", 2002, Proc. Natl. Acad. Sci., USA, 99(suppl. 4): 16433-16437. [5 pages].

Chung et al. "A 5' Element of the Chicken p-Globin Domain Serves as an Insulator in Human Erythroid Cells and Protects against Position Effect in *Drosophila*", 1993; Cell 74:505-514. [10 pages].

Chung et al. "Characterization of the chicken β-globin insulator", PNAS 94:575-580; 1997. [6 pages].

Clever et al. "RNA Secondary Structure and Binding Sites for gag Gene Products in the 59 Packaging Signal of Human Immunodeficiency Virus Type 1", J. of Virology, 1995, vol. 69, No. 4; pp. 2101-2109. [9 pages].

Cullen and Greene. "Regulatory pathways governing HIV-1 replication", Cell 58 (3): 423-426 (1989). [4 pages].

Cullen et al. "Human Immunodeficiency Virus as a Prototypic Complex Retrovirus", 1991, J. Virol. 65:3, pp. 1053-1056. [4 pages].

Donello et al. "Woodchuck Hepatitis Virus Contains a Tripartite Posttranscriptional Regulatory Element", Journal of Virology, vol. 72, No. 6, p. 5085-5092, Jun. 1998. [8 pages].

Dull et al. "A Third-Generation Lentivirus Vector with a Conditional Packaging System", Journal of Virology, 1998, 72 (11), p. 8463-8471 [9 pages].

Fan et al.: "Association Between Negative Results From Tests for HBV DNA and RNA and Durability of Response After Discontinuation of Nucles(t)ide Analogue Therapy", Clinical Gastroenterology and Hepatology, vol. 18, No. 3, 2020, pp. 719-727. [16 pages].

(Continued)

*Primary Examiner* — Jeffrey S Parkin
(74) *Attorney, Agent, or Firm* — LEASON ELLIS LLP

(57) ABSTRACT

The present disclosure provides methods for rapidly assaying the titer of an RNA viral vector such as a lentiviral vector. The method can be used to quickly evaluate the titer of intermediate products in various steps of a lentiviral vector production process.

19 Claims, 5 Drawing Sheets

Specification includes a Sequence Listing.

(56) References Cited

OTHER PUBLICATIONS

Huang et al., "Hepatitis B Virus RNA Element That Facilitates Accumulation of Surface Gene Transcripts in the Cytoplasm", J. Virol., 1994, vol. 68, No. 5:3193-3199. [7 pages].
Huang et al. "Cellular Proteins That Bind to the Hepatitis B Virus Posttranscriptional Regulatory Element", Virology 217, 573-581 (1996). [9 pages].
Huang et al., "Role of the Hepatitis B Virus Posttranscriptional Regulatory Element in Export of Intronless Transcripts", Mol. Cell Biol. 1995, 15(7): 3864-3869. [6 pages].
Husemoen et al.: "Application of the polymerase chain reaction in determination of recombinant retrovirus titers as fifty percent end-points", APMIS, vol. 108, No. 1, 2000, pp. 38-44 [7 pages].
Liu et al. "HnRNP L binds a cis-acting RNA sequence element that enables intron-independent gene expression", 1995, Genes Dev., 9:1766-1780. [15 pages].
Lu and Cullen. "Analysis of the stimulatory effect of splicing on mRNA production and utilization in mammalian cells", RNA (2003) 9:618-630. [14 pages].
Malim et al., "HIV-1 Structural Gene Expression Requires the Binding of Multiple Rev Monomers to the Viral RRE: Implications for HIV-1 Latency", Cell, 65, 241-248 (1991). [8 pages].
Nakamura et al.: "Epstein-Barr-virus-infected human T-cell line with a unique pattern of viral-gene expression", International Journal of Cancer, vol. 76, No. 4, 1998, pp. 587-594. [8 pages].
Naldini. "Lentiviruses as gene transfer agents for delivery to non-dividing cells", Curr Opin Biotech (1998) 9:457-463. [7 pages].
Naldini et al. "In Vivo Gene Delivery and Stable Transduction of Nondividing Cells by a Lentiviral Vector", Science 272: 263-267 (1996). [5 pages].
Rickels et al. "An Evolutionary Conserved Epigenetic Mark of Polycomb Response Elements Implemented by Trx/MLL/COMPASS", Mol Cell (2016) 63, 318-328. [12 pages].
Zennou et al. "HIV-1 Genome Nuclear Import Is Mediated by a Central DNA Flap", Cell, vol. 101:173-185, 2000 [13 pages].
Zhan et al. "Insulator: from chromatin domain boundary to gene regulation", Hum. Genet. (2001), 109:471-478 [8 pages].
Zufferey et al. "Multiply attenuated lentiviral vector achieves efficient gene delivery in vivo", Nature Biotechnology, vol. 15, 1997, pp. 871-875. [5 pages].
Zufferey et al. "Woodchuck Hepatitis Virus Posttranscriptional Regulatory Element Enhances Expression of Transgenes Delivered by Retroviral Vectors", J. Virol., 1999, vol. 73, No. 4:2886-2892. [7 pages].
Gregory Lizée: "Real-time quantitative reverse transcriptase-polymerase chain reaction as a method for determining lentiviral vector titers and measuring transgene expression": Human Gene Therapy, 2003, 14,6:497-507. 11 pages.
Zhang et al.: "A Real-Time Fluorescence Quantitative PCR Method for Detecting Lentivirus Titer", Letters in Biotechnology, vol. 30, No. 4, 2019, pp. 523-527. 6 pages.

* cited by examiner

METHOD FOR DETERMINING TITER OF RNA VIRAL VECTORS

CROSS REFERENCE TO RELATED APPLICATION

The present application claims priority to Chinese patent application No. 2020109229562, filed Sep. 4, 2020, which is hereby incorporated by reference in its entirety.

SEQUENCE LISTING

This application contains a Sequence Listing which has been filed electronically in ASCII format and is hereby incorporated by reference in its entirety. Said ASCII copy, created on Sep. 2, 2021, is named 11299-009941-WO0_ST25.txt and is 2 KB in size.

TECHNICAL FIELD

The present disclosure relates to methods for rapidly determining the titer of RNA viral vectors, such as lentiviral vectors.

BACKGROUND

Gene therapy refers to the introduction of an exogenous therapeutic gene into target cells to correct or compensate for a disease caused by a gene defect or abnormality. Alternatively, a product expressed by the exogenous gene can act on a therapeutic target for treatment.

Exogenous genes can be transduced or delivered through viral or non-viral vectors. Commonly used non-viral vectors include liposomes, dendrimers, non-natural cationic polymers, natural polysaccharides, and the like. Non-viral gene delivery vectors are relatively safe and stable, but their transfection efficiency is usually low. Viral vectors can package foreign genes into the capsids of natural viruses, and use the infectivity of the virus to introduce the foreign genes into cells. Common viral vectors include retroviruses (recombinant retrovirus, rRV), recombinant lentiviruses (rLV), adenoviruses (recombinant adenovirus, rAd), and adeno-associated viruses (recombinant adeno-associated virus, rAAV). The transduction efficiency of viral vectors is much higher than that of non-viral vectors. Thus, viral vectors are especially suitable for infecting difficult-to-infect target cells, such as lymphocytes.

Recombinant lentiviral vectors can be based on HIV-1 (human immunodeficiency type I virus). Different from the other retroviral vectors, lentiviral vectors have the ability to infect both dividing and non-dividing cells. Recombinant lentiviral vectors have become the first-choice transgenic vectors for CAR-T cells and gene therapy due to their high biological titers and low immunogenicity in vivo and in vitro.

At present, the most common assays for determining the titer of recombinant lentiviral vectors include the p24 Elisa method and the functional titer quantitative method. The p24 Elisa method takes one day to produce results, while the latter requires at least 7 days and can be non-specific.

Therefore, there is an urgent need to develop a method for rapidly assessing the titer of lentiviral vectors.

SUMMARY

The present disclosure provides for a method for determining a titer of an RNA viral vector in a sample. The method may comprise: (a) providing a sample comprising an RNA viral vector and DNA molecules, or adding DNA molecules to a sample comprising an RNA viral vector, wherein both the RNA viral vector and the DNA molecules comprise a sequence element; (b) obtaining a first portion and a second portion from the sample; and (c) performing polymerase chain reaction (PCR) on the first portion to determine a copy number of the sequence element in the first portion (n1), and performing reverse transcription PCR (RT-PCR) on the second portion to determine a copy number of the sequence element in the second portion (n2), wherein an RNA copy number of the RNA viral vector in the sample is determined by a difference between n1 and n2 which is n2−n1.

The method may further comprise step (d) determining an infectious titer of the RNA viral vector based on the RNA copy number of the RNA viral vector in the sample.

The method may further comprise step (d) determining the titer of the RNA viral vector based on the RNA copy number in the sample.

The RNA viral vector may be a retroviral vector, such as a lentiviral vector.

The sequence element may be a regulatory element, such as a woodchuck hepatitis virus posttranscriptional regulatory element (WPRE).

The sequence element may be a long terminal repeat (LTR) or a promoter.

The PCR may use a primer pair to amplify a region of the sequence element. The RT-PCR may use a primer pair to amplify a region of the sequence element.

The PCR and the RT-PCR may use a primer pair to amplify a region of the sequence element, respectively.

The primer pair may comprise two primers comprising nucleotide sequences set forth in: (i) SEQ ID NO: 1 and SEQ ID NO: 2, respectively; (ii) SEQ ID NO: 3 and SEQ ID NO: 4, respectively; or (iii) SEQ ID NO: 5 and SEQ ID NO: 6, respectively.

The PCR may be quantitative PCR (qPCR). The RT-PCR may be RT-qPCR (real-time quantitative reverse transcription PCR).

The DNA molecules may be DNA plasmids. In one embodiment, the DNA plasmids are packaging plasmids, envelope plasmids, and/or transfer plasmids.

In certain embodiments, the infectious titer of the RNA viral vector is determined by: (the RNA copy number of the RNA viral vector×an infectious titer of a positive control)/a RNA copy number of the positive control, wherein the positive control is an RNA viral vector with a known infectious titer.

The titer of the RNA viral vector may be determined within 2 hours.

The titer may be a physical titer or an infectious titer.

The present disclosure provides a method for rapidly determining the titer of an RNA viral vector (e.g., a lentiviral vector).

A first aspect of the present disclosure provides a method for rapidly determining the titer (e.g., infectious titer or physical titer) of an RNA viral vector (e.g., a lentiviral vector), the method comprising:

(a) providing a sample to be tested, wherein the sample comprises the RNA viral vector (e.g., the lentiviral vector) and DNA molecules (e.g., DNA plasmid);

(b) performing RT-PCR and PCR reactions on the sample respectively to obtain copy numbers of a sequence element (e.g., the WPRE element) in the sample, wherein the copy numbers of the sequence element (e.g., the WPRE element) comprises an RNA copy number of the RNA viral vector (e.g., the lentiviral vector) containing the sequence element (e.g., the WPRE element) and a copy number of the DNA molecules (e.g., DNA plasmid) containing the sequence element (e.g., the WPRE element); and (c) determining the titer of the RNA viral vector (e.g., the lentiviral vector) based on the RNA copy number of the RNA viral vector (e.g., the lentiviral vector) containing the sequence element (e.g., the WPRE element) in the sample.

In one embodiment, the RNA copy number of the RNA viral vector (e.g., the lentiviral vector) containing the sequence element (e.g., the WPRE element) in the sample may be calculated using the following formula: a total copy number of the RNA copy number of the RNA viral vector (e.g., the lentiviral vector) containing the sequence element (e.g., the WPRE element) and the copy number of the DNA molecules (e.g., DNA plasmid) containing the sequence element (e.g., the WPRE element)–the copy number of the DNA molecules (e.g., DNA plasmid) containing the sequence element (e.g., the WPRE element). The total copy number is obtained using RT-PCR, whereas the copy number of the DNA molecules is obtained using PCR.

The symbol "–" refers to subtracting to obtain a difference.

In one embodiment, "based on the RNA copy number of the RNA viral vector" in step (c) comprises performing calculation using formula Q1 to obtain the titer of the RNA viral vector (e.g., the lentiviral vector):

$$Q1=(\text{copy number of viral vector RNA in the sample}*\text{titer of a positive control})/\text{copy number of the viral vector RNA in the positive control}.$$

The positive control refers to an RNA viral vector (e.g., a lentiviral vector) with a known titer (e.g., infectious titer or physical titer). The methods of assaying the titer of the positive control and the RNA copy number in the positive control may the same as the methods of assaying the those of the sample to be tested.

The RNA copy number of the RNA viral vector (e.g., the lentiviral vector) in the sample to be tested may be obtained with the following formula: the total copy number of the RNA copy number of the RNA viral vector (e.g., the lentiviral vector) containing the sequence element (e.g., the WPRE element) and the copy number of the DNA molecules (e.g., DNA plasmid) containing the sequence element (e.g., the WPRE element)–the copy number of the DNA molecules (e.g., DNA plasmid) containing the sequence element (e.g., the WPRE element). The total copy number is obtained using RT-PCR, whereas the copy number of the DNA molecules is obtained using PCR.

In one embodiment, the titer is an infectious titer or functional titer. In another embodiment, the titer is a physical titer.

In certain embodiments, the sample to be tested is from, or derived from, an RNA viral vector (e.g., a lentiviral vector) packaging supernatant, a purified intermediate product, or a final product in the RNA viral vector (e.g., the lentiviral vector) research and development, and production process.

In one embodiment, the PCR includes real-time PCR, quantitative PCR, quantitative real-time PCR or qPCR. quantitative PCR, for example, using SYBR green dye (Thermo Fisher Scientific). The qPCR may be real-time PCR with double-stranded DNA-binding dyes as reporters (non-specific detection). In one embodiment, the PCR is quantitative PCR using SYBR green dye. The qPCR may be real-time PCR with fluorescent reporter probe method (specific detection). In one embodiment, the PCR is TaqMan real time PCR.

In certain embodiments, the RT-PCR may similarly be RT-qPCR as described herein.

In one embodiment, in an RT-PCR reaction, a primer pair (e.g., an upstream primer and a downstream primer) is used to specifically amplify the sequence element (e.g., the WPRE element) on the RNA viral vector (e.g., the lentiviral vector), and on the DNA molecules (e.g., DNA plasmid), thereby obtaining cycle threshold (Ct) values for specifically amplifying the sequence element (e.g., the WPRE element) on the RNA viral vector (e.g., the lentiviral vector) and on the DNA molecules (e.g., DNA plasmid).

In one embodiment, the upstream primer and downstream primer are used to amplify the sequence element (e.g., the WPRE element) in a PCR or RT-PCR.

In certain embodiments, the upstream primer and downstream primer are as shown below.

```
Primer pair 1:
Upstream primer:
                          (SEQ ID NO: 1)
actgtgtttgctgacgcaac;

Downstream primer:
                           SEQ ID NO: 2)
acaacaccacggaattgtca.

Primer pair 2:
Upstream primer:
                          (SEQ ID NO: 3)
actgtgtttgctgacgcaac;

Downstream primer:
                          (SEQ ID NO: 4)
gatgatttccccgacaacac.

Primer pair 3:
Upstream primer:
                          (SEQ ID NO: 5)
gtgttgtcggggaaatcatc;

Downstream primer:
                          (SEQ ID NO: 6)
gagatccgactcgtctgagg
```

In one embodiment, in a PCR reaction, a primer pair (e.g., an upstream primer and a downstream primer) is used to specifically amplify the sequence element (e.g., the WPRE element) on the DNA molecules (e.g., plasmid DNA), thereby obtaining a Ct value for specifically amplifying the sequence element (e.g., the WPRE element) on the DNA molecules (e.g., plasmid DNA).

In certain embodiments, the upstream primer and downstream primer are as shown below.

```
Primer pair 1:
Upstream primer:
                        (SEQ ID NO.: 1)
actgtgtttgctgacgcaac;

Downstream primer:
                        (SEQ ID NO.: 2)
acaacaccacggaattgtca.

Primer pair 2:
Upstream primer:
                        (SEQ ID NO.: 3)
actgtgtttgctgacgcaac;
```

-continued

```
Downstream primer:
                    (SEQ ID NO.: 4)
gatgatttccccgacaacac.

Primer pair 3:
Upstream primer:
                    (SEQ ID NO.: 5)
gtgttgtcggggaaatcatc;

Downstream primer:
                    (SEQ ID NO.: 6)
gagatccgactcgtctgagg.
```

In one embodiment, based on the Ct value of the specific amplification of the sequence element (e.g., the WPRE element) of the DNA molecules (e.g., plasmid DNA), a copy number of the DNA molecules (e.g., plasmid DNA) is obtained.

In certain embodiments, the copy number of the sequence element (e.g., the WPRE element) obtained after PCR is identical (or substantially identical) to the copy number of the DNA molecules (e.g., plasmid DNA).

In certain embodiments, the copy number of the sequence element (e.g., the WPRE element) obtained after RT-PCR is identical (or substantially identical) to a total of the RNA copy number of the RNA viral vector (e.g., the lentiviral vector) and the copy number of the DNA molecules (e.g., plasmid DNA).

In one embodiment, the Ct values of the specific amplification of the sequence element (e.g., the WPRE element) on the RNA viral vector (e.g., the lentiviral vector) and on the DNA molecules (e.g., plasmid DNA) are used to calculate the total copy number of the RNA viral vector (e.g., the lentiviral vector) RNA and the DNA molecules (e.g., plasmid DNA) using formula Q2.

*Q*2=copy number of RNA and/or DNA=(copy number of nucleic acid of the sample in each reaction well×1000×dilution factor)/amount of the sample added to each reaction well.

The copy number of the nucleic acid of the sample in each reaction well=$10^{\wedge(aX+b)}$, where X is the average of the Ct values of the sample; a is the coefficient obtained by standard curve fitting; and b is the intercept obtained by the standard curve fitting.

In one embodiment, based on (i) the total copy number of the RNA viral vector (e.g., the lentiviral vector) RNA and the DNA molecules (e.g., plasmid DNA) and (ii) the copy number of the DNA molecules (e.g., plasmid DNA), formula Q3 is used to calculate the copy number of the RNA viral vector (e.g., the lentiviral vector) RNA in the sample to be tested.

*Q*3=total copy number of the RNA viral vector (e.g., the lentiviral vector) RNA and the DNA molecules (e.g., plasmid DNA)−copy number of the DNA molecules (e.g., plasmid DNA).

In one embodiment, the upstream and downstream primers that are used to specifically amplify the sequence element (e.g., the WPRE element) are from the detection kit of Lenti-X™ qRT-PCR Titration Kit (Takara).

In one embodiment, the DNA plasmid is, or is derived from, a packaging plasmid. In one embodiment, the DNA plasmid is, or is derived from, an envelope plasmid. In one embodiment, the DNA plasmid is, or is derived from, a transfer plasmid.

In one embodiment, the method also uses a positive control.

In one embodiment, the method is a non-diagnostic and non-therapeutic method.

In one embodiment, the method is an in vitro method.

In one embodiment, the concentration of the RNA viral vector (e.g., the lentiviral vector) in the sample to be tested is $5\times10^5$-$5\times10^9$ transducing units/ml (TU/ml), $1\times10^6$-$8\times10^8$ TU/ml, or $5\times10^6$-$5\times10^8$ TU/ml.

It should be understood that within the scope of the present disclosure, the above-mentioned technical features and the technical features specifically described in the following (such as the embodiments) can be combined with each other to form a new or preferred technical solution.

DETAILED DESCRIPTION

Figure 1:
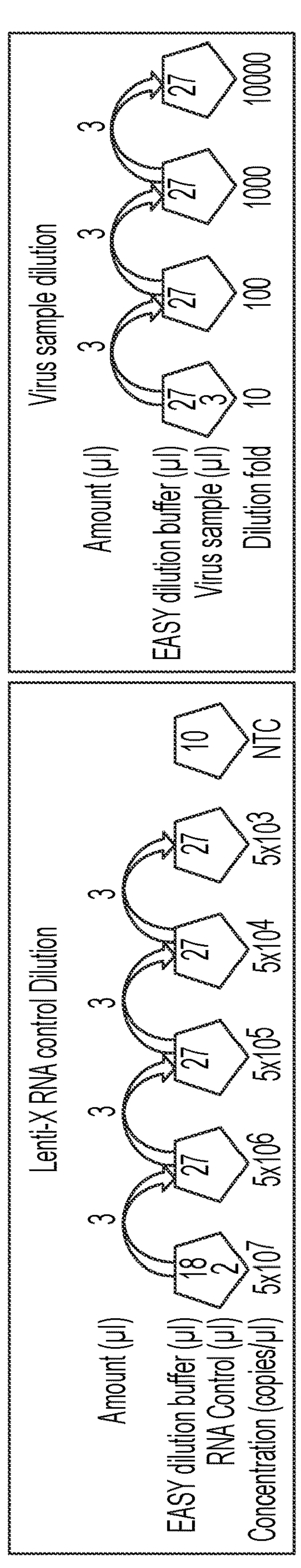
FIG. 1 shows a preparation process of the serial dilution for the lentivirus standard (with known copy number; left panel) and sample (right panel). In the left panel, the lentivirus standard provided by the kit had a concentration of $5\times10^8$ copies/μl. First, 2 μl of $5\times10^8$ copies/μ1 lentivirus standard was transferred into a clean EP tube, then 18 μl of the EASY dilution buffer was added and mixed well. 3 μl of the mixed solution (having a concentration of $5\times10^7$ copies/μl) was then added to 27 μl of the EASY dilution buffer and mixed well. According to the above procedure, five lentivirus standard concentrations were prepared. NTC was the EASY dilution buffer alone. The right panel shows the dilution process of the sample to be tested.

The present disclosure provides for a method for determining a titer of an RNA viral vector in a sample. The method may comprise: (a) providing a sample comprising an RNA viral vector and DNA molecules, or adding DNA molecules to a sample comprising an RNA viral vector, wherein both the RNA viral vector and the DNA molecules comprise a sequence element; (b) obtaining a first portion and a second portion from the sample; and (c) performing polymerase chain reaction (PCR) on the first portion to determine a copy number of the sequence element in the first portion (n1), and performing reverse transcription PCR (RT-PCR) on the second portion to determine a copy number of the sequence element in the second portion (n2), wherein an RNA copy number of the RNA viral vector in the sample is determined by a difference between n1 and n2 which is n2−n1.

The method may further comprise step (d) determining an infectious titer of the RNA viral vector based on the RNA copy number of the RNA viral vector in the sample.

The method may further comprise step (d) determining the titer of the RNA viral vector based on the RNA copy number in the sample.

The RNA viral vector may be a retroviral vector, such as a lentiviral vector.

The sequence element may be a regulatory element, such as a woodchuck hepatitis virus posttranscriptional regulatory element (WPRE).

The sequence element may be a long terminal repeat (LTR) or a promoter.

The PCR may use a primer pair to amplify a region of the sequence element. The RT-PCR may use a primer pair to amplify a region of the sequence element.

The PCR and the RT-PCR may use a primer pair to amplify a region of the sequence element, respectively.

The primer pair may comprise two primers comprising nucleotide sequences set forth in: (i) SEQ ID NO: 1 and SEQ ID NO: 2, respectively; (ii) SEQ ID NO: 3 and SEQ ID NO: 4, respectively; or (iii) SEQ ID NO: 5 and SEQ ID NO: 6, respectively.

The PCR may be quantitative PCR (qPCR). The RT-PCR may be RT-qPCR.

The DNA molecules may be DNA plasmids. In one embodiment, the DNA plasmids are packaging plasmids, envelope plasmids, and/or transfer plasmids.

In certain embodiments, the infectious titer of the RNA viral vector is determined by: (the RNA copy number of the RNA viral vector×an infectious titer of a positive control)/a RNA copy number of the positive control, wherein the positive control is an RNA viral vector with a known infectious titer.

The titer of the RNA viral vector may be determined within 2 hours.

The titer may be a physical titer or an infectious titer.

Physical titers measure the amount of viral particles in a sample and may be based on the presence of viral nucleic acid, or a viral protein, such as p24. Functional titers, or infectious titers, measure how many of the viral particles produced can actually infect cells. Assays for infectious titers may involve infecting a target cell line with the virus and assaying for expression of a gene or quantifying the number of viral copies that have integrated into the target cell's genome.

In certain embodiments, physical titers may be evaluated based on the viral RNA copy number. In one embodiment, the physical titer is the viral RNA copy number per ml or µ1. The physical titer can be determined by quantitative PCR, for example, using SYBR green dye, or by TaqMan PCR. Viral genome copy number in a 1 ml sample can be calculated from a standard curve generated from serial dilutions of a standard nucleic acid (e.g., an RNA standard, an RNA viral standard such as a lentiviral standard), e.g., with known copy number.

In certain embodiments, infectious titers may be determined based on the infectious units determined by proviral integration titer assay. For example, infectious titers may be determined through transduction of cells with serial dilutions of the RNA viral vector and calculation of the copies of integrated vector per cell by quantitative PCR (e.g., TaqMan PCR).

In certain embodiments, for biosafety reasons, the RNA viral genome (e.g., lentiviral genome) has been modified and cis and trans-acting viral sequences have been segregated over 3 to 4 different plasmids. For example, viral structural and functional proteins can be provided in trans and are encoded by 1 or 2 packaging plasmids while the envelope plasmid encodes the glycoprotein of the vesicular stomatitis virus envelope (VSV-G) and a transfer plasmid encodes the transgene of interest flanked by all cis-acting viral sequences necessary for packaging of the RNA genome. Production of lentiviral vectors may be achieved by transient transfection of cells, e.g., human embryonic kidney (293T) cells, using high concentrations of the different plasmids, implicating the presence of residual plasmid DNA in the vector preparation, even after concentration.

In certain embodiments, an RNA viral vector (e.g., lentiviral vector) sample may also contain DNA molecules (e.g., plasmid DNA). In certain embodiments, an RNA viral vector (e.g., lentiviral vector) sample does not contain DNA molecules (e.g., plasmid DNA).

In certain embodiments, the present method may comprise adding DNA molecules to a sample comprising an RNA viral vector. When added to the sample, the DNA molecules may have a concentration ranging from about 102 copies/µl to about $10^8$ copies/µl, from about 103 copies/µl to about $10^8$ copies/µl, from about $10^4$ copies/µl to about $10^8$ copies/µl, from about $10^5$ copies/µl to about $10^8$ copies/µl, from about $10^6$ copies/µl to about $10^8$ copies/µl, from about 103 copies/µl to about $10^7$ copies/µl, from about $10^4$ copies/µl to about $10^7$ copies/µl, from about $10^5$ copies/µl to about $10^7$ copies/µl, from about $10^6$ copies/µl to about $10^7$ copies/µl, from about 103 copies/µl to about $10^6$ copies/µl, from about $10^4$ copies/µl to about $10^6$ copies/µl, from about $10^5$ copies/µl to about $10^6$ copies/µl, from about 102 copies/µl to about 103 copies/µl, from about 102 copies/µl to about $10^4$ copies/µl, from about 102 copies/µl to about $10^5$ copies/µl, from about 102 copies/µl to about $10^6$ copies/µl, from about 103 copies/µl to about $10^4$ copies/µl, from about 103 copies/µl to about $10^5$ copies/µl, from about 103 copies/µl to about $10^6$ copies/µl, from about $10^4$ copies/µl to about $10^7$ copies/µl, from about $10^4$ copies/µl to about $10^6$ copies/µl, or from about $10^4$ copies/µl to about $10^5$ copies/µl.

In certain embodiments, the titer (infectious titer or physical titer) of the RNA viral vector equals: (the RNA copy number in the sample*a titer of a positive control)/a RNA copy number of the positive control, wherein the positive control is an RNA viral vector with a known titer (infectious titer or physical titer). The symbol "*" refers to multiplying. The symbol "I" refers to dividing.

The present disclosure provides a method for determining a titer of an RNA viral vector (e.g., a lentiviral vector) in a sample. The method may comprise: (a) providing a sample, wherein the sample comprises the RNA viral vector (e.g., lentiviral vector) and free plasmid DNA; (b) performing RT-PCR and PCR reactions on the sample respectively to obtain a copy number of a WPRE element in the sample, wherein the copy number of the WPRE element comprises a copy number of the lentiviral vector RNA containing the WPRE element and a copy number of the free plasmid DNA containing the WPRE element; and (c) determining the titer of the lentiviral vector based on the copy number of the lentiviral vector RNA.

The present method provides several advantages. The present method can rapidly determine the titer of an RNA viral vector (e.g., lentiviral vector), e.g., within two hours. It can be used to evaluate quickly and quantitatively the titer of intermediate products in the RNA viral vector (e.g., lentiviral vector) production process, and can help control the quantity of the final product of a viral vector. The sequence element (e.g., the WPRE element) may be amplified by a quantitative method, e.g., RT-PCR. The copy number of the DNA molecules (e.g., plasmid DNA) and the copy number of the RNA viral vector (e.g., lentiviral vector) RNA in the sample can be determined. By subtracting the copy number of the DNA molecules (e.g., plasmid DNA) from the total copy number of the DNA molecules (e.g., plasmid DNA) and the RNA viral vector (e.g., lentiviral vector) RNA, the titer of the RNA viral vector (e.g., lentiviral vector) can be determined quickly and specifically. In addition, the experimental design and operation of the present method are simple. Thus, the assay for the titer of the RNA viral vector (e.g., lentiviral vector) can be carried out quickly, effectively and specifically within two hours. The present method may use the titer of a positive control to calculate the titer of a sample, which can help adjust the amount of the viral vector quickly. The present method provides simple operation steps, short detection time, fast feedback of detection results, and highly reliable results. It is very suitable for the determination of the titer of RNA viral vectors (e.g., lentiviral vectors) at different stages in the development or production process of RNA viral vectors (e.g., lentiviral vectors).

In certain embodiments, RT-PCR and PCR are performed respectively on a sample containing an RNA viral vector. RT-PCR amplifies both the vector RNA and the DNA, whereas PCR (without a reverse transcriptase) only amplifies the DNA. The copy number of the viral vector (RNA) can be calculated by the difference between (i) the total copy number of the viral vector (RNA) containing the sequence element (e.g., the WPRE element) and the copy number of the DNA (e.g., plasmid DNA), obtained by RT-PCR, and (ii) the copy number of the DNA (e.g., plasmid DNA) containing the sequence element (e.g., the WPRE element), obtained by PCR.

Based on the RNA copy number of the RNA viral vector (e.g., lentiviral vector) in the sample, the titer (e.g., infectious titer) of the RNA viral vector (e.g., lentiviral vector) can be determined.

Moreover, the present method can substantially decrease non-specific interference from plasmids or other nucleic acids, and quickly achieve quantification. Furthermore, the present method can produce specific quantitative results within 2 hours, which can be used to evaluate the titer of intermediate products quickly and quantitatively in a lentiviral vector production process. In addition, the physical titer or functional titer of the final product can be controlled in the implementation.

The term "vector" is used herein to refer to a nucleic acid molecule capable of transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., retroviruses and lentiviruses.

The term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles may include various viral components and sometimes also host cell components in addition to nucleic acid(s). The term "viral vector" may refer either to a virus or viral particle capable of transferring a nucleic acid into a cell or to the transferred nucleic acid itself. Viral vectors and transfer plasmids contain structural and/or functional genetic elements that are primarily derived from a virus.

Cycle threshold value (Ct) may refer to the cycle number at which a significant increase in fluorescence above baseline signal is detected.

The term "about" in reference to a numeric value refers to ±10% of the stated numeric value. In other words, the numeric value can be in a range of 90% of the stated value to 110% of the stated value.

RNA Viruses and Retroviruses

An RNA virus is a virus that has RNA (ribonucleic acid) as its genetic material. This nucleic acid may be single-stranded RNA (ssRNA) or double-stranded RNA (dsRNA).

RNA viruses include, but are not limited to, Astroviridae, Caliciviridae, Picornaviridae, Coronoviridae, Retroviridae, Togaviridae, Alphatetraviridae, Birnaviridae, Cystoviridae, Nodaviridae, and Permutotretraviridae and Flaviviridae. As examples, the Astroviridae family includes the human astrovirus; the Caliciviridae family includes the Norwalk virus; the Picornaviridae family includes coxsackievirus, the Hepatitis A virus, poliovirus, rhinovirus, bymovirus, comovirus, nepovirus, nodavirus, picornavirus, potyvirus, sobemovirus and a subset of luteoviruses (such as beet western yellows virus and potato leafroll virus); the Coronoviridae family includes coronavirus and the SAR virus; the Retroviridae family includes alpharetrovirus, betaretrovirus, deltaretrovirus, lentivirus, and spumavirus; the Togaviridae family includes the Rubella virus and the alpha virus; and the flaviviridae family includes the Hepatitis C virus, flavivirus, Carmoviruses, dianthoviruses, pestiviruses, statoviruses, tombusviruses, single-stranded RNA bacteriophages, and a subset of luteoviruses (barley yellow dwarf virus).

In certain embodiments, the RNA virus may be a Coronaviridae family virus, a Pneumoviridae family virus, a Paramyxoviridae family virus, a Picornaviridae family virus, or a Orthomyxoviridae family virus. In certain embodiments, the Coronaviridae family virus is Coronavirus or SARS, the Pneumoviridae family virus is human respiratory syncytial virus (HRSV), the Paramyxoviridae family virus is human parainfluenza virus, measles virus or mumps virus, the Picornaviridae family virus is rhinovirus, and the Orthomyxoviridae family virus is influenza virus. In certain embodiments, the RNA virus is a Pneumoviridae family virus. In one embodiment, the RNA virus is HRSV.

Non-limiting examples of RNA viruses also include human respiratory syncytial virus, Ebola virus, coronavirus, rhinovirus, parainfluenza virus, human immunodeficiency virus, rotavirus, picobirnavirus, Bluetongue virus, Alphavirus, carlavirus, furovirus, hordeivirus, potexvirus, rubivirus, tobravirus, tricornavirus, tymovirus, apple chlorotic leaf spot virus, beet yellows virus, hepatitis E virus, celivirus, deltavirus, emaravirus, higrevirus, idaeovirus, ourmiavirus, polemovirus, sobemovirus, tenuivirus, umbravirus, varicosavirus etc. The RNA virus may be from a virus taxonomic Order such as Mononegavirales, Nidovirales, Picornavirales, and Tymovirales.

Retroviruses

A retrovirus is an RNA virus that reverse transcribes its genomic RNA into a DNA copy and subsequently integrates the DNA into a host genome. Once the virus is integrated into the host genome, it is referred to as a provirus. The provirus serves as a template for RNA polymerase and directs the expression of RNA molecules which encode the structural proteins and enzymes needed to produce new viral particles.

The family Retroviridae can be divided into two subfamilies: Orthoretrovirinae and Spumaretrovirinae. Subfamily Orthoretrovirinae includes the following genera: Alpharetrovirus (such as Avian leukosis virus and Rous sarcoma virus); Betaretrovirus (such as Mouse mammary tumor virus); Gammaretrovirus (such as Murine leukemia virus and Feline leukemia virus); Deltaretrovirus (such as Bovine leukemia virus and the cancer-causing Human T-lymphotropic virus); Epsilonretrovirus; and Lentivirus (such as Human immunodeficiency virus 1 and Simian and Feline immunodeficiency viruses). Subfamily Spumaretrovirinae includes the following genera: Bovispumavirus; Equispumavirus; Felispumavirus; Prosimiispumavirus; and Simiispumavirus.

Non-Limiting examples of retroviruses include: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

The term "retroviral vector" refers to a viral vector or plasmid containing structural and functional genetic elements, or portions thereof, that are primarily derived from a retrovirus. The terms "retroviral vector" and "retrovirus" may be used interchangeably.

The term "retrovirus" or "retroviral vector", as used herein is meant to include "lentivirus" and "lentiviral vectors".

Lentiviruses

Lentiviruses include, but are not limited to, HIV (human immunodeficiency virus; including HIV type 1, and HIV type 2); visna-maedi virus (VMV); caprine arthritis-encephalitis virus (CAEV); equine infectious anemia virus (EIAV); feline immunodeficiency virus (FIV); bovine immune deficiency virus (BIV); and simian immunodeficiency virus (SIV).

The term "lentiviral vector" refers to a viral vector or plasmid containing structural and functional genetic elements, or portions thereof, including long terminal repeats (LTRs) that are primarily derived from a lentivirus. In particular embodiments, the term "lentiviral vector" may be used to refer to lentiviral transfer plasmids and/or infectious lentiviral particles.

The terms "lentiviral vector" and "lentivirus" may be used interchangeably.

Sequence Elements

In PCR or RT-PCR, primers targeting a sequence element may be used to amplify the sequence element. Sequence elements include specific viral components, cloning sites, promoters, control elements, regulatory elements, heterologous nucleic acids (e.g., the transgene itself), etc. Non-limiting examples of the sequence element include LTRs, WPRE, promoters, etc. Promoters include the CMV promoter, the U6 promoter, the PGK promoter, etc.

Where reference is made herein to a sequence element, it is to be understood that the sequences of these elements are present in RNA form in the RNA viral vectors or RNA viruses (e.g., lentiviral vectors or lentiviruses) and are present in DNA form in the DNA molecules (e.g., plasmids).

The "control elements" or "regulatory elements" may be those non-translated regions of the vector, such as origin of replication, selection cassettes, promoters, enhancers, translation initiation signals (e.g., Shine Dalgarno sequence, Kozak sequence), introns, a polyadenylation sequence, 5' and 3' untranslated regions, which interact with host cellular proteins to carry out transcription and/or translation.

In certain embodiments, the sequence element may be a regulatory element, such as a posttranscriptional regulatory element, a polyadenylation site, a transcription termination signal, etc. In certain embodiments, the sequence element may be woodchuck hepatitis virus posttranscriptional regulatory element (WPRE). In certain embodiments, the sequence element may be the posttranscriptional regulatory element present in hepatitis B virus (HPRE). In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, J. Virol., 73:2886); the posttranscriptional regulatory element present in hepatitis B virus (HPRE) (Huang et al., Mol. Cell. Biol., 5:3864); and the like (Liu et al., 1995, Genes Dev., 9:1766). In particular embodiments, vectors of the invention comprise a posttranscriptional regulatory element such as a WPRE or HPRE.

For example, WPRE may refer to a region similar to the human hepatitis B virus posttranscriptional regulatory element (HBVPRE) present in the Woodchuck hepatitis virus genomic sequence (GenBank Accession No. J04514), and that the 592 nucleotides from position 1093 to 1684 of this genomic sequence correspond to the post-transcriptional regulatory region (Journal of Virology, Vol. 72, p. 5085-5092, 1998). The analysis using retroviral vectors revealed that WPRE inserted into the 3'-terminal untranslated region of a gene of interest increases the amount of protein produced. It has also been reported that the introduction of WPRE suppresses mRNA degradation (Journal of Virology, Vol. 73, p. 2886-2892, 1999).

In certain embodiments, the sequence element may be a regulatory element, such as an intron, an enhancer element, etc. Regulatory sequences useful herein may also contain an intron, such as one located between the promoter/enhancer sequence and the coding sequence. One exemplary intron sequence is derived from SV40, and is referred to as the SV40 intron. Other enhancer elements that can be used in the vectors include, e.g., ubiquitin enhancer and CMB enhancer. Additional regulatory elements that can be used include, e.g., aptazyme, miRNA and miRNA binding elements.

In certain embodiments, the sequence element may be an LTR. At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site). In various embodiments, vectors comprise modified 5' LTR and/or 3' LTRs. Either or both of the LTR may comprise one or more modifications including, but not limited to, one or more deletions, insertions, or substitutions. Modifications of the 3' LTR are often made to improve the safety of lentiviral or retroviral systems by rendering viruses replication-defective. "Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment, the 3' LTR is modified such that the U5 region is replaced, for example, with an ideal poly(A) sequence. It should be noted that modifications to the LTRs such as modifications to the 3' LTR, the 5' LTR, or both 3' and 5' LTRs, are also included in the present disclosure.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system.

In certain embodiments, the sequence element may be a packaging sequence. As used herein, the term "packaging signal" or "packaging sequence" refers to sequences located within the retroviral genome which are required for insertion of the viral RNA into the viral capsid or particle, see e.g., Clever et al., 1995. J. of Virology, Vol. 69, No. 4; pp. 2101-2109. Several retroviral vectors use the minimal packaging signal (also referred to as the psi [Ψ] sequence) needed for encapsidation of the viral genome. Thus, as used herein, the terms "packaging sequence," "packaging signal," "psi" and the symbol "Ψ" are used in reference to the non-coding sequence required for encapsidation of retroviral RNA strands during viral particle formation.

In certain embodiments, the sequence element may be a TAR element. In certain embodiments, viral vectors comprise a TAR element which may be the sequence element. The term "TAR" refers to the "trans-activation response" genetic element located in the R region of lentiviral (e.g., HIV) LTRs. This element interacts with the lentiviral trans-activator (tat) genetic element to enhance viral replication.

In certain embodiments, the sequence element may be the R region. The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

In certain embodiments, the sequence element may be the FLAP element. As used herein, the term "FLAP element" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, Cell, 101:173. During HIV-1 reverse transcription, central initiation of the plus-strand DNA at the central polypurine tract (cPPT) and central termination at the central termination sequence (CTS) lead to the formation of a three-stranded DNA structure: the HIV-1 central DNA flap. In particular embodiments, the retroviral or lentiviral vector backbones comprise one or more FLAP elements upstream or downstream of the heterologous genes of interest in the vectors. For example, in particular embodiments a transfer plasmid includes a FLAP element. In one embodiment, a vector of the present disclosure comprises a FLAP element isolated from HIV-1.

In certain embodiments, the sequence element may be the export element. In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. J. Virol. 65: 1053; and Cullen et al., 1991. Cell 58: 423), and the hepatitis B virus post-transcriptional regulatory element (HPRE). Generally, the RNA export element is placed within the 3' UTR of a gene, and can be inserted as one or multiple copies.

In certain embodiments, the sequence element may be the transcription termination signal or polyadenylation sequence. Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Illustrative examples of polyA signals include an ideal polyA sequence (e.g., AATAAA, ATTAAA, AGTAAA), a bovine growth hormone polyA sequence (BGHpA), a rabbit beta-globin polyA sequence (rβgpA), or another suitable heterologous or endogenous polyA sequence known in the art. Polyadenylation sequences also include SV40 PolyA, bGH PolyA and a synthetic PolyA tail.

In certain embodiments, the sequence element may be the insulator element. In certain embodiments, a retroviral or lentiviral vector further comprises one or more insulator elements. Insulator elements may contribute to protecting lentivirus-expressed sequences, e.g., therapeutic polypeptides, from integration site effects, which may be mediated by cis-acting elements present in genomic DNA and lead to deregulated expression of transferred sequences (i.e., position effect; see, e.g., Burgess-Beusse et al., 2002, Proc. Natl. Acad. Sci., USA, 99:16433; and Zhan et al., 2001, Hum. Genet., 109:471). In some embodiments, transfer vectors comprise one or more insulator element the 3' LTR and upon integration of the provirus into the host genome, the provirus comprises the one or more insulators at both the 5' LTR or 3' LTR, by virtue of duplicating the 3' LTR. Suitable insulators for use in the invention include, but are not limited to, the chicken beta-globin insulator (see Chung et al., 1993. Cell 74:505; Chung et al., 1997. PNAS 94:575; and Bell et al., 1999. Cell 98:387, incorporated by reference herein). Examples of insulator elements include, but are not limited to, an insulator from a beta-globin locus, such as chicken HS4.

In certain embodiments, the sequence element may be heterologous nucleic acids, such as an antibiotic resistance gene, GFP (green fluorescent protein), the transgene, etc.

It is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid of the present disclosure.

RT-PCR

RT-PCR (reverse transcription-polymerase chain reaction) is a technology that combines reverse transcription (RT) of RNA and polymerase chain amplification (PCR) of cDNA. First, cDNA is synthesized from RNA by a reverse transcriptase, and then the target fragment is amplified and synthesized by a DNA polymerase using the cDNA as a template. RT-PCR technology is sensitive and versatile, and can be used to detect gene expression levels in cells and the content of RNA viruses in cells or culture supernatants. In certain embodiments, an RT-PCR reaction system may contain a primer(s), a reverse transcriptase, a PCR enzyme, a buffer, dNTPs and other components.

For RT-PCR, viral RNA is first converted to cDNA and then quantified using PCR (e.g., real-time PCR, quantitative PCR or qPCR).

In the present disclosure, RT-PCR may be used to detect both the DNA and RNA in the same sample.

Figure 6:
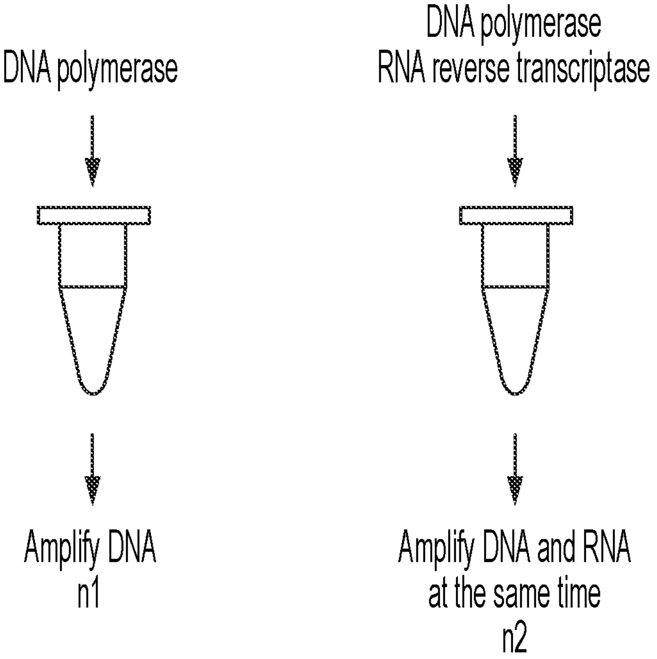
FIG. 6 is a setup of the reaction tube (RT-PCR) and the control tube (PCR), where RT-PCR and PCR reactions are performed, respectively. The copy number of nucleic acids can be calculated by absolute quantification. The nucleic acid copy number (RNA+DNA) of the sample in the reaction tube (RT-PCR) is labeled as n2 (which is the total copy number of the nucleic acid). The copy number of the nucleic acid (DNA, e.g., plasmid DNA) in the control tube is labeled as n1 (which is the copy number of DNA), and n2−n1=RNA copy number of RNA viral vector (e.g., lentiviral vector).

In one embodiment, a reaction tube and a control tube are provided. The reaction tube contains the sample to be tested and all the reaction systems of RT-PCR. The control tube contains the same sample as in the reaction tube, and the PCR reaction system (e.g., the RT-PCR reaction system except for the reverse transcriptase). In the reaction tube, RNA and DNA will both be amplified to obtain the Ct value of the specifically amplified sequence element (e.g., the WPRE element). The copy number calculated for the reaction tube is the RNA copy number of the RNA viral vector (e.g., lentiviral vector) plus the copy number of the DNA molecules (e.g., plasmid DNA). In the control tube, without the reverse transcriptase, the RNA of the RNA viral vector (e.g., lentiviral vector) cannot be amplified, and only the DNA molecules (e.g., plasmid DNA) are amplified to obtain the Ct value of the specific amplified sequence element (e.g., the WPRE element). The copy number obtained therefrom is the DNA copy number of the DNA molecules (e.g., plasmid DNA). Next, the RNA copy number of the RNA viral vector (e.g., lentiviral vector) can be obtained by subtracting the copy number of the DNA in the control tube (n1) from the copy number of the RNA and DNA in the reaction tube (n2), i.e., n2−n1=RNA copy number of the RNA viral vector (e.g., lentiviral vector) (as shown in FIG. 6).

Positive Control

The positive control may be a viral vector (e.g., an RNA viral vector such as a lentiviral vector) with a known titer, infectious titer or physical titer (for example, LV-CAR001, obtained from Shanghai CBMG Biotechnology Co., Ltd.).

In certain embodiments, the positive control also contains DNA and RNA, and the calculation method of the copy number and titer of the positive control is the same as the calculation formulae of the sample to be tested.

The present invention may be better understood by reference to the following non-limiting examples, which are presented in order to more fully illustrate the preferred embodiments of the invention. The present disclosure will be further explained below in conjunction with certain specific embodiments. It should be understood that these embodiments are only used to illustrate the present invention and not to limit the scope of the present invention. The experimental methods that do not specify specific conditions in the following examples are usually based on corresponding conventional conditions, for example, the conditions described in Sambrook et al., Molecular Cloning: Laboratory Manual (New York: Cold Spring Harbor Laboratory Press, 1989), or according to the conditions recommended by the manufacturers. Unless otherwise stated, the percentages and parts are calculated by weight.

Unless otherwise specified, the reagents and materials used in the example of the present disclosure are all commercially available products.

Example 1

Devices: Quantstudio™ DX (ABI)

1. Reagent Preparation

The experiments were carried out on ice. A sufficient volume of Master Reaction Mix (MRM) was prepared.

| | Volume/well (μl) | |
|---|---|---|
| Reagent | Positive control | Experimental group |
| RNase-Free Water | 6.8 | 7.2 |
| PCR Buffer (2X) | 10.0 | 10.0 |
| Lenti-X Forward Primer (10 μM) | 0.4 | 0.4 |
| Lenti-X Reverse Primer (10 μM) | 0.4 | 0.4 |
| PCR enzyme | 0.4 | 0.4 |
| RT Enzyme Mix | 0.4 | N/A |
| Total | 18.4 | 18.4 |

2. Sample Dilution

The sample to be tested was diluted with the EASY dilution buffer to an appropriate concentration ($10^5$-$10^9$ TU/ml).

3. Sample Lysis

2 μl of the diluted virus and 18 μl of a virus lysis buffer were added, mixed well, and incubated at room temperature for 1 to 5 min.

4. Establishment of a standard curve using Lenti-X RNA Control dilution template The standard dilution was carried out in a clean 0.2 ml PCR tube. A serial dilution of the RNA standard was performed with reference to FIG. 1. Each tube was thoroughly mixed before the next tube was diluted. $5\times10^7$ copies/μl was used as the highest point of the standard curve, and the EASY dilution buffer was used as the negative control (NTC, 0 copies/0).

5. A 96-well PCR plate was placed on ice. 18.4 μl of MRM (three parallel samples) was transferred to an appropriate well with a pipette.

6. A pipette was used to transfer 1.6 μl of the standard dilution, NTCs, and samples (three parallel samples) to the 96-well PCR plate.

7. Centrifuge at 2000 rpm at 4° C. for 2 minutes to remove air bubbles.

8. A PCR program was set up according to FIG. 2. The 96-well plate was loaded to start the program.

9. Data Processing

1) Standard curve: The average Ct value of Lenti-X RNA Control gradient dilution was linearly related to the RNA copy number (log scale).

2) The RNA copy number of the sample in each reaction well was calculated based on the average Ct value of the diluted sample. The Ct average value obtained from the serial dilution samples of the lentivirus standard in the kit was used as the X-axis. The corresponding logarithmic value of the lentivirus standard RNA copy number was used as the Y-axis. The standard curve was obtained by fitting, with the calculation formula being Y=aX+b.

Y: Logarithmic value (with base 10) of the RNA copy number of RNA standard or the lentiviral vector to be tested X: The average of Ct values obtained from the standard or the sample a: Coefficient obtained by standard curve fitting b: Intercept obtained by standard curve fitting A (copy number of nucleic acid in each reaction well)=$10^{\wedge(aX+b)}$ 3) The copy number of RNA of the original sample (copies/ml)=$5\times10^7$ copies/ul Results:

1. Standard Curve

A standard curve was prepared with a standard (e.g., RNA standard) of known copy number to calculate the copy number of unknown samples. The dilution of the Lenti-X RNA standard and the dilution of the virus sample were carried out as shown in FIG. 1. The program shown in FIG. 2 was used for PCR amplification. A standard curve was plotted based on the Ct value and the corresponding virus copy number (FIG. 3). By means of measuring the standard product, the obtained detection value can be fitted. The fitted data showed a good linear correlation ($R^2\geq0.9999$), indicating that the detection method had good stability and accuracy.

2. Melting Curve

Figure 4:
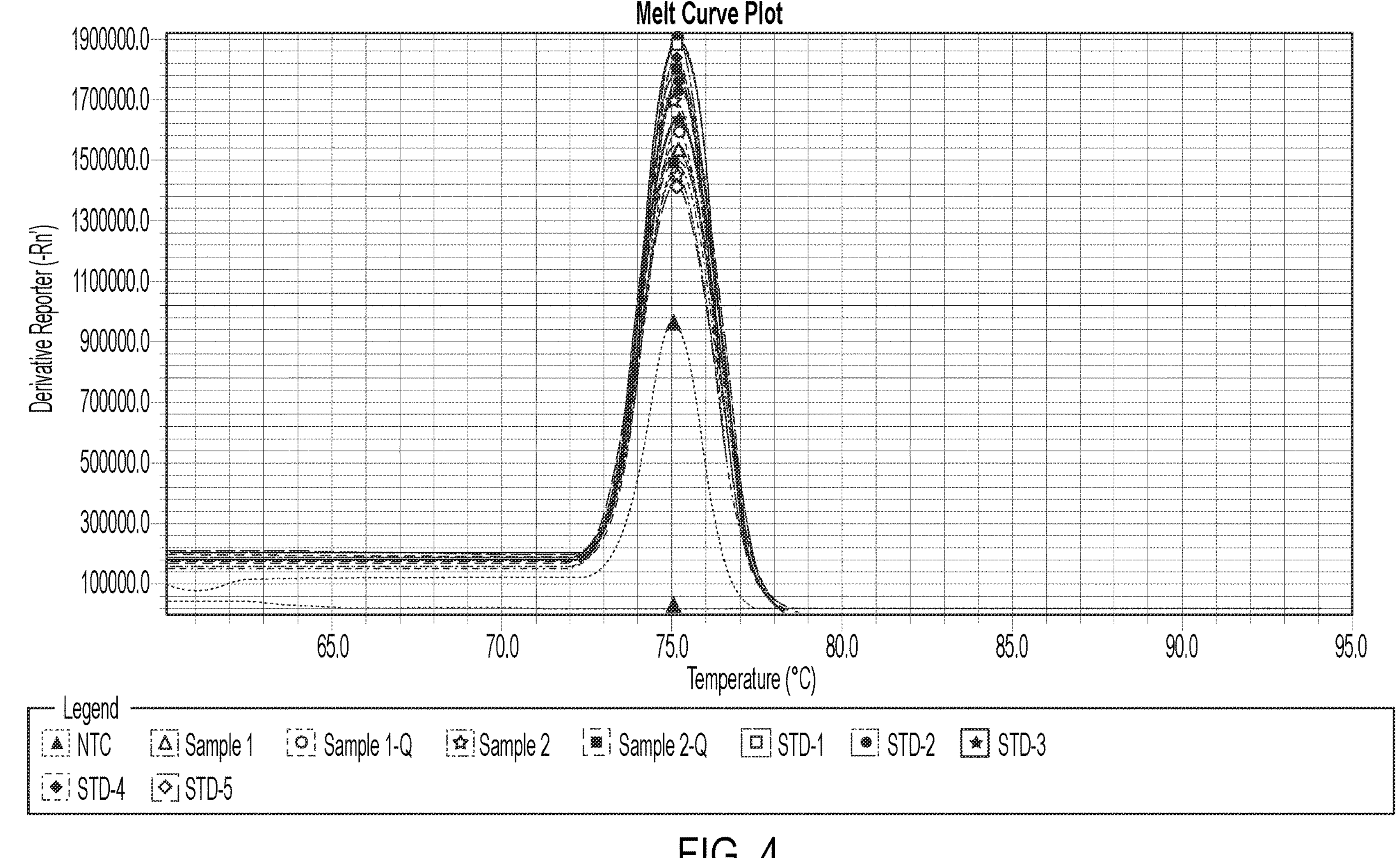
FIG. 4 is the melting curve of a product obtained by specific amplification of the WPRE element and the plasmid DNA using the upstream and downstream primers as described herein. The melting curve has only one sharp peak, indicating that the primers have good specificity.

The melting curve (FIG. 4) can verify the specificity of the amplified product and the condition of the product, by studying the number of peaks and the positions of the peaks. Different peaks represent different products. If there are two peaks or even multiple peaks, it indicates that the specificity of the primers is not high, that is, the Ct value obtained is not reliable. Here, the melting curve obtained by the real-time quantitative PCR reaction had only one sharp peak, indicating that the primers in this reaction system had high specificity. The product amplified by the present method was stable and accurate, and the detection data was reliable.

Figure 5:
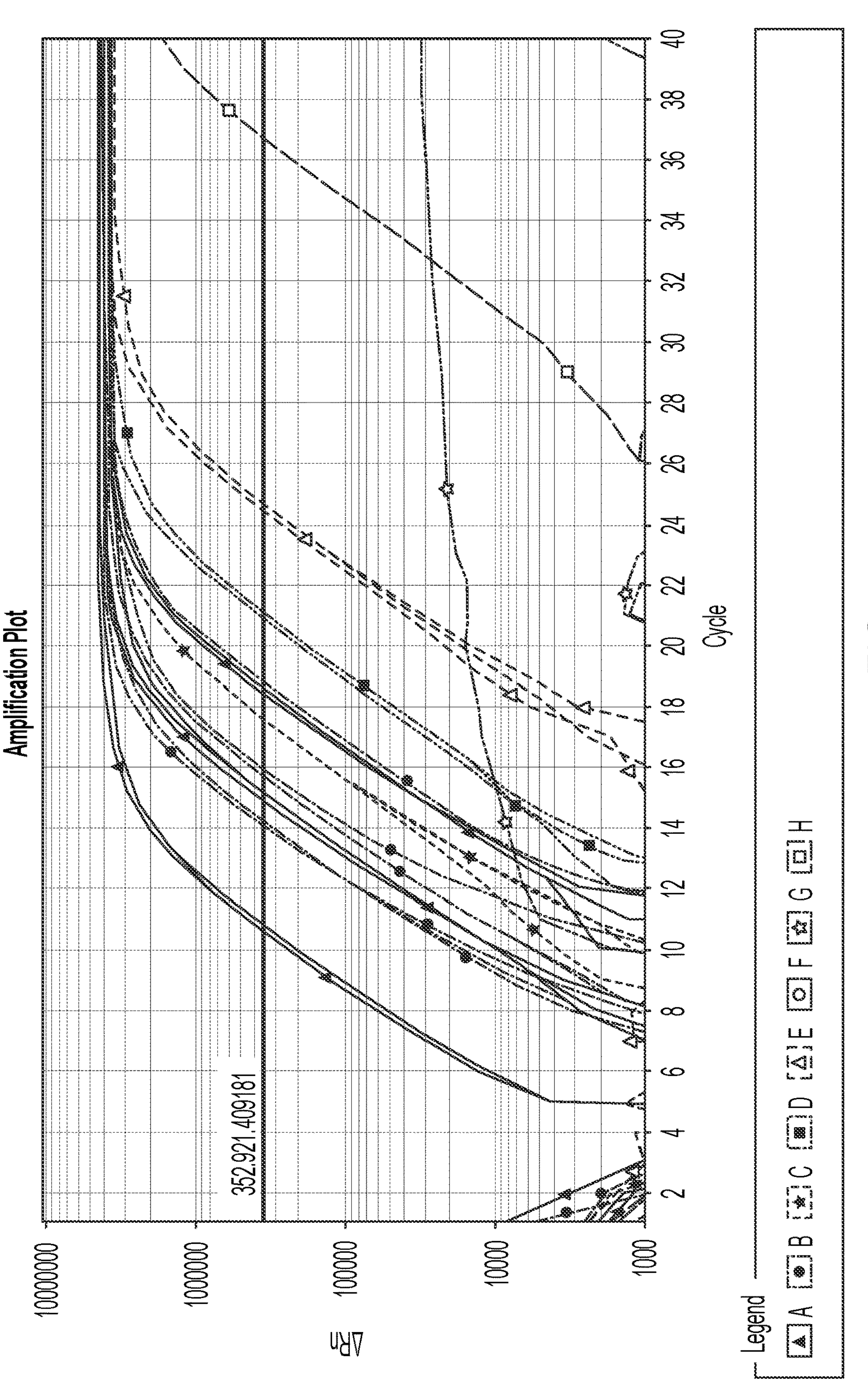
FIG. 5 is the amplification curve of a real-time quantitative PCR reaction. The amplification curves have similar/same slope and are substantially parallel, indicating consistent efficiency of the primers. There was no contamination that inhibited PCR in the reaction wells (except for the NTC curve).

3. Amplification Curve (FIG. 5)

The amplification curve of real-time quantitative PCR can reflect the amplification efficiency of the reaction. High and consistent amplification efficiency is the key to successful detection. If the amplification efficiency is inconsistent, the slope of the amplification efficiency curve will not have the same slope and will not be parallel, indicating that the efficiency of the primers is not the same, or there is contamination that inhibits PCR in individual samples or reaction wells. It can be seen from FIG. 5 that the amplification curves obtained by using the present method were substantially parallel and the degree of inclination was similar or substantially identical, indicating that the method of the present invention had a high amplification efficiency.

4. Calculation Results

| | Sample to be tested | | Control sample | |
|---|---|---|---|---|
| Sample Name | Sample 1 | Sample 1-Q | Sample 2 | Sample 2-Q |
| Ct Mean | 15.085 | 18.462 | 15.742 | 18.611 |
| Ct SD | 0.158 | 0.096 | 0.135 | 0.145 |
| Quantity Mean | 4.19E+06 | 4.44E+05 | 2.71E+06 | 4.03E+05 |
| Quantity SD | 4.47E+05 | 2.89E+04 | 2.41E+05 | 3.77E+04 |
| Tm1 | 75.072 | 75.170 | 75.072 | 75.072 |
| Dilution factor | 10 | 10 | 10 | 10 |
| Quantity (Copies/ml) | 2.62E+11 | 2.78E+10 | 1.69E+11 | 2.52E+10 |
| Tier: Copies/ml (minus Q sample) | 2.34E+11 | | 1.44E+11 | |
| Infectious tier (TU/ml) | 2.28E+08 | | 1.40E+08 | |

It can be seen from the Ct SD value that the samples to be tested were substantially parallel to each other. The melting temperatures (Tm) of the products after specific amplification were all around 75° C., indicating good primer amplification efficiency, and there was no non-specific amplification. By comparing with the positive control with known infectious titer, the infectious titer of the sample can also be quickly and calculated/estimated. It is of great significance to obtain the lentivirus titer of samples in a timely manner. It shows that this method has good applicability for rapid detection of lentivirus titers.

Figure 2:
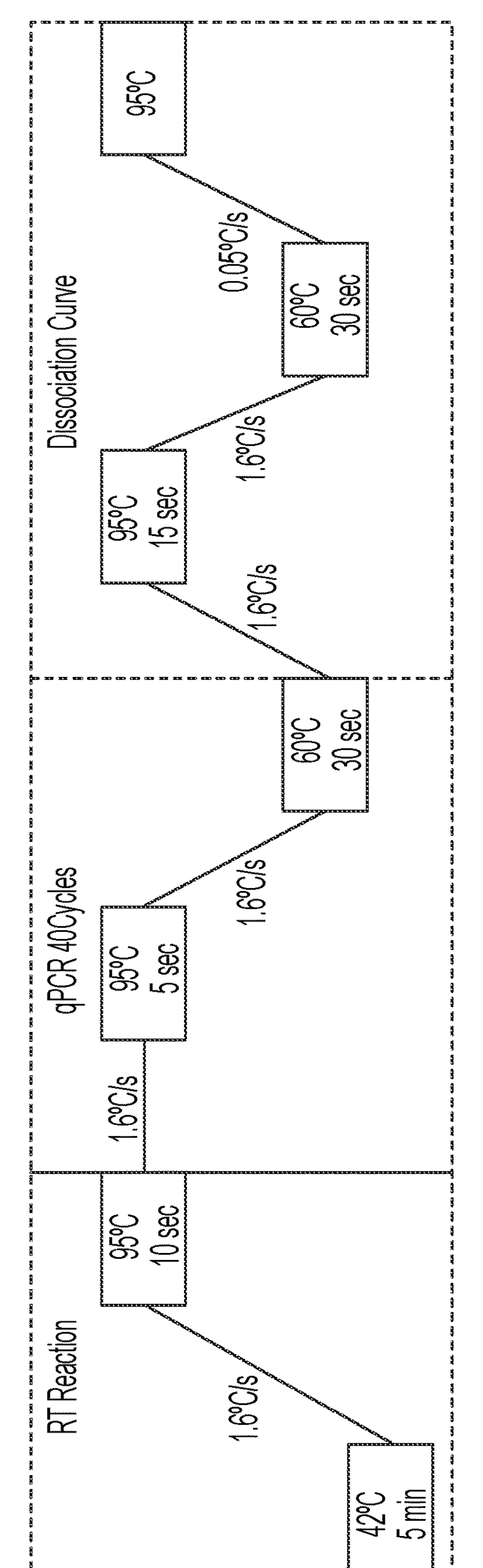
FIG. 2 is the parameters for the qPCR, showing the temperature and time settings.
Figure 3:
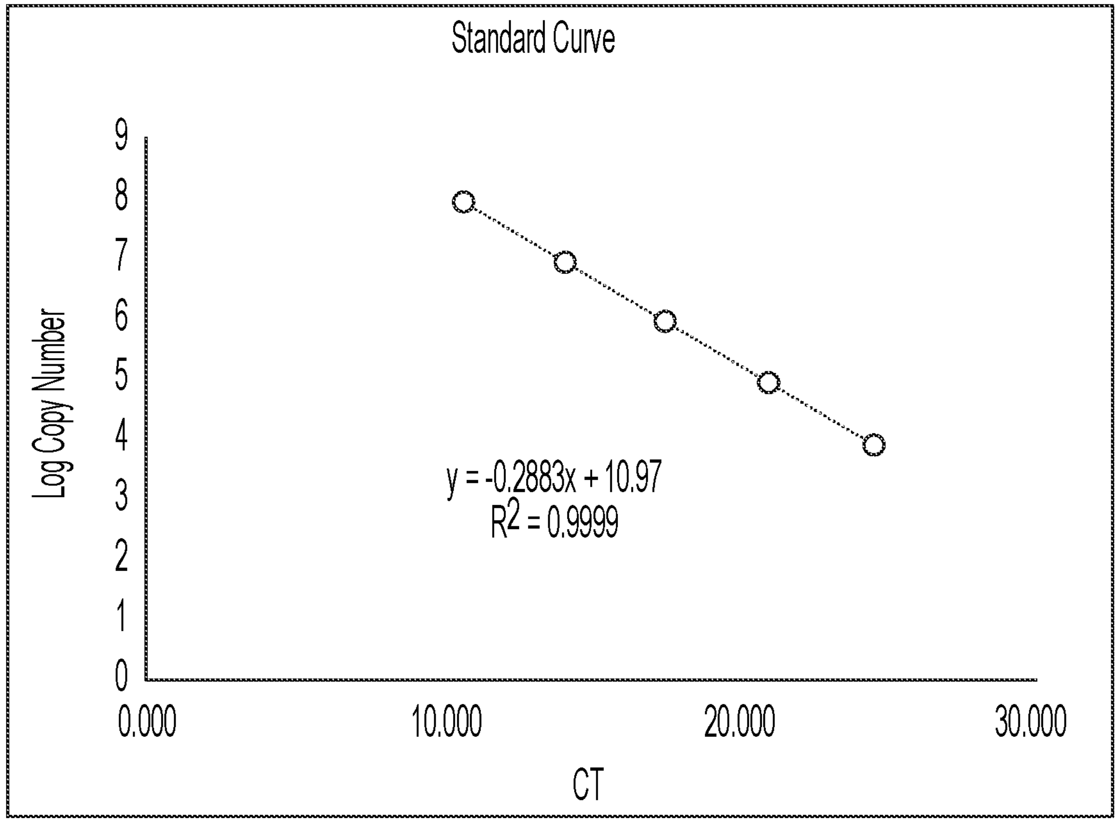
FIG. 3 is a standard curve plotted with the Ct average values obtained from the serially diluted samples of the lentivirus standard as the x-axis, and the logarithm (with base 10) of the corresponding copy number of the lentivirus standard as the y-axis. The following calculation formula was obtained: $y=-0.5883x+10.97$, $R^2=0.9999$. It can be seen from this formula that with this detection method, the logarithmic value of the lentiviral RNA copy number had a good linear correlation with the corresponding Ct value. The testing method was stable and reliable. The standard curve can be used to calculate the copy number of a lentivirus sample.

The parameters of the qPCR program are shown in FIG. 2. The total time from the start to the end of the program is 1 hour and 20 minutes. When combined with the sample preparation time and the data processing time after the qPCR program, the total time can be within 2 hours.

CONCLUSION

Normally, it may take 3 to 7 days to determine the infectious titer of a lentiviral vector. As the lentiviral vectors are fragile and easy to be degraded, a fast-titering method need to be developed for in-process monitoring during lentiviral vector manufacturing. Using the present method, the infectious titer (or physical titer) of the lentiviral vector can be determined efficiently, quickly (e.g., within 2 hours) and specifically. The method can be used to quickly determine the titer of the intermediate samples in the production process, to determine the amount of the intermediate product, and to control the concentration of the final product.

The scope of the present disclosure is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present disclosure and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present disclosure have been shown and described, it will be obvious to those skilled in the art that changes and modifications may be made without departing from the spirit and scope of the invention. The matter set forth in the foregoing description and accompanying drawings is offered by way of illustration only and not as a limitation.

The invention claimed is:

1. A method for determining a titer of an RNA viral vector in a sample, the method comprising:

(a) providing a sample comprising an RNA viral vector and DNA molecules, or adding DNA molecules to a sample comprising an RNA viral vector, wherein both the RNA viral vector and the DNA molecules comprise a sequence element;

(b) obtaining a first portion and a second portion from the sample; and (c) performing polymerase chain reaction (PCR) on the first portion to determine a copy number of the sequence element in the first portion (n1), and performing reverse transcription PCR (RT-PCR) on the second portion to determine a copy number of the sequence element in the second portion (n2), wherein an RNA copy number of the RNA viral vector in the sample is determined by a difference between n1 and n2 which is n2−n1.

2. The method of claim 1, further comprising (d) determining the titer of the RNA viral vector based on the RNA copy number of the RNA viral vector in the sample.

3. The method of claim 1, wherein the RNA viral vector is a retroviral vector.

4. The method of claim 3, wherein the retroviral vector is a lentiviral vector.

5. The method of claim 1, wherein the sequence element is a regulatory element.

6. The method of claim 5, wherein the regulatory element is a woodchuck hepatitis virus posttranscriptional regulatory element (WPRE).

7. The method of claim 1, wherein the sequence element is a long terminal repeat (LTR) or a promoter.

8. The method of claim 1, wherein the PCR uses a primer pair to amplify a region of the sequence element.

9. The method of claim 1, wherein the RT-PCR uses a primer pair to amplify a region of the sequence element.

10. The method of claim 1, wherein the PCR and the RT-PCR use a primer pair to amplify a region of the sequence element, respectively.

11. The method of claim 8, wherein the primer pair comprises two primers comprising nucleotide sequences set forth in: (i) SEQ ID NO: 1 and SEQ ID NO: 2, respectively; (ii) SEQ ID NO: 3 and SEQ ID NO: 4, respectively; or (iii) SEQ ID NO: 5 and SEQ ID NO: 6, respectively.

12. The method of claim 1, wherein the PCR is quantitative PCR (qPCR), and the RT-PCR is RT-qPCR.

13. The method of claim 1, wherein the titer is a physical titer or an infectious titer.

14. The method of claim 1, wherein the DNA molecules are DNA plasmids.

15. The method of claim 14, wherein the DNA plasmids are packaging plasmids.

16. The method of claim 2, wherein the titer of the RNA viral vector is determined by: (the RNA copy number of the RNA viral vector×an infectious titer of a positive control)/a RNA copy number of the positive control, wherein the positive control is an RNA viral vector with a known infectious titer.

17. The method of claim 2, wherein the titer of the RNA viral vector is determined within 2 hours.

18. The method of claim 9, wherein the primer pair comprises two primers comprising nucleotide sequences set forth in: (i) SEQ ID NO: 1 and SEQ ID NO: 2, respectively; (ii) SEQ ID NO: 3 and SEQ ID NO: 4, respectively; or (iii) SEQ ID NO: 5 and SEQ ID NO: 6, respectively.

19. The method of claim 10, wherein the primer pair comprises two primers comprising nucleotide sequences set forth in: (i) SEQ ID NO: 1 and SEQ ID NO: 2, respectively; (ii) SEQ ID NO: 3 and SEQ ID NO: 4, respectively; or (iii) SEQ ID NO: 5 and SEQ ID NO: 6, respectively.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
actgtgtttg ctgacgcaac 20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
acaacaccac ggaattgtca 20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
actgtgtttg ctgacgcaac 20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gatgatttcc ccgacaacac 20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
gtgttgtcgg ggaaatcatc 20

<210> SEQ ID NO 6
<211> LENGTH: 20
<212> TYPE: DNA

-continued

```
<213> ORGANISM: Artificial Sequence
<220> FEATURE:
<223> OTHER INFORMATION: Synthetic

<400> SEQUENCE: 6

gagatccgac tcgtctgagg                                          20
```